US005352456A

United States Patent [19]

Fallon et al.

[11] Patent Number: 5,352,456

[45] Date of Patent: Oct. 4, 1994

[54] DEVICE FOR ADMINISTERING DRUG TRANSDERMALLY WHICH PROVIDES AN INITIAL PULSE OF DRUG

[75] Inventors: Renee A. Fallon, Sunnyvale; Donald R. Wilson, San Francisco, both of Calif.

[73] Assignee: Cygnus Therapeutic Systems, Redwood City, Calif.

[21] Appl. No.: 775,638

[22] Filed: Oct. 10, 1991

[51] Int. Cl.[5] .................................... A61F 13/02

[52] U.S. Cl. .................................... 424/448; 424/447; 424/449

[58] Field of Search ................ 424/448, 449, 447, 443

[56] References Cited

U.S. PATENT DOCUMENTS

| | | | |
|---|---|---|---|
| 4,060,084 | 11/1977 | Chandrasekran et al. | 128/260 |
| 4,379,454 | 4/1983 | Campbell et al. | 424/449 |
| 4,460,372 | 7/1984 | Campbell et al. | 424/449 |
| 4,698,062 | 10/1987 | Gale et al. | 604/896 |
| 4,906,463 | 3/1990 | Cleary et al. | 424/449 |
| 4,927,632 | 5/1990 | Wong | 424/422 |
| 4,956,181 | 9/1990 | Bayer et al. | 424/447 |

OTHER PUBLICATIONS

Kondo, S., et al., *J. Pharmacobio-Dyn.* (1987) 10:662-668.

*Primary Examiner*—Thurman K. Page
*Assistant Examiner*—D. Gabrielle Phelan
*Attorney, Agent, or Firm*—Morrison & Foerster

[57] ABSTRACT

A transdermal drug delivery device that administers drug in an initial pulse followed by a substantially lower continuous rate comprising a drug reservoir of the drug dissolved in a carrier and a volatile permeation enhancer confined between a backing that is permeable to the volatile permeation enhancer and an underlying substrate layer that is permeable to the drug, carrier and enhancer. When the device is placed on the skin the volatile permeation enhancer is depleted from the reservoir by evaporation through the backing such that the magnitude and duration of the pulse is dependent upon the permeability of the backing layer to the volatile enhancer.

17 Claims, 4 Drawing Sheets

10
11
12
13
14
15
16

DEVICE FOR ADMINISTERING DRUG TRANSDERMALLY WHICH PROVIDES AN INITIAL PULSE OF DRUG

DESCRIPTION

1. Technical Field

This invention is in the field of medical devices for administering drugs transdermally. More particularly, it concerns a transdermal drug delivery device whose structure and composition is such that it administers the drug with an initial pulse or burst of drug.

2. Background

The efficacy of some systemically acting drugs may be optimized by administering them in a manner that produces therapeutically effective blood levels rapidly. The most common such method of administration is bolus injection. Oral administration, depending upon the ability of the drug to be absorbed into circulation via the gastrointestinal tract, may also afford a rapid onset of therapeutically effective blood levels.

Transdermal drug delivery, while often viewed as an advantageous mode of administration over injection or oral dosing, is not normally considered to be a practical means for achieving high blood levels of drug rapidly. This is because most transdermal devices operate in a manner that results in a significant lag time between placing the device on the skin and realizing the required or desired blood levels.

There are, however, two prior transdermal device designs that have been proposed for providing an initial burst or pulse of drug. The first of these designs is described in U.S. Pat. No. 4,060,084. It involves use of a drug reservoir layer in which the bulk of the drug is contained, an underlying rate-controlling membrane that controls the release rate of the drug from the reservoir, and a basal adhesive layer that is loaded with drug. When this type of device is placed on the skin, the drug in the adhesive migrates rapidly into the skin providing a "burst." The burst is followed by the controlled delivery of drug from the reservoir via the rate-controlling membrane. The second design is described in U.S. Pat. No. 4,698,062. It uses a first reservoir which contains a sufficient amount of the drug to provide a baseline flux over the entire administration period and a second reservoir which contains a permeation enhancer in an amount that is sufficient to provide enhancement only during the beginning of the administration period. With this design, the magnitude and duration of the period of enhanced drug flux is apparently dependent only upon the amount of enhancer contained in the second reservoir and its effect on skin flux. The patent indicates that this pattern of drug release may be achieved with various enhancers including ethanol, n-decylmethylsulfoxide, dimethyl lauramide, and polyethylene glycol monolaurate.

A principal object of the present invention is to provide a transdermal drug delivery device that releases drug with an initial burst or pulse via a mechanism that is totally different from those of the above-described devices.

DISCLOSURE OF THE INVENTION

The present invention is a device for administering a drug through intact skin that provides an initial pulse in the flux of the drug through the skin followed by a substantially lower flux of drug through the skin comprising in combination:

(a) a reservoir comprising the drug and a volatile permeation enhancer;

(b) a backing layer overlying the reservoir that is permeable to the volatile permeation enhancer; and (c) means for maintaining the device on the skin in drug and permeation enhancer transferring relationship thereto, whereby when the device is placed on the skin, the volatile permeation enhancer is depleted from the reservoir by evaporation through the backing layer with the magnitude and duration of the pulse being dependent inter alia upon the permeability of the backing layer to the enhancer.

MODES FOR CARRYING OUT THE INVENTION

Figure 1:
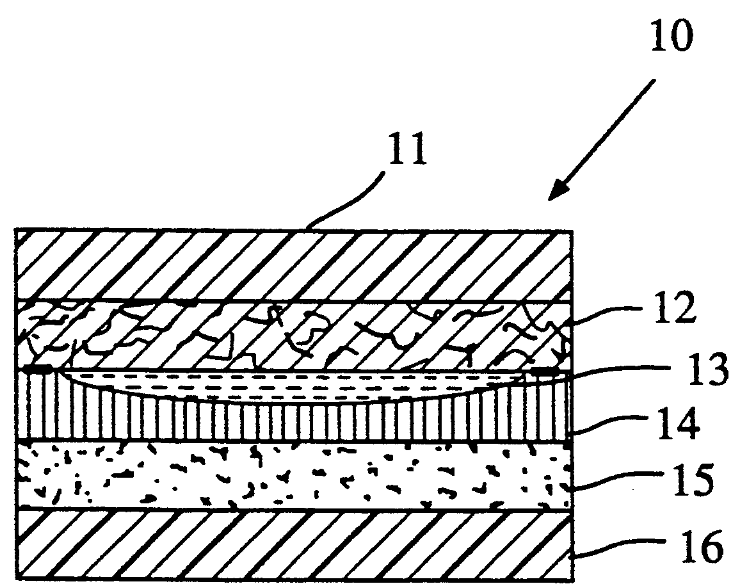
FIG. 1 is an elevated cross-section (not to scale) of one embodiment of the invention.

As used herein the term "drug" intends a biologically active compound or mixture of compounds that has a therapeutic, prophylactic or other beneficial effect on the wearer of the device. Drugs whose efficacy is facilitated by being administered in a manner that provides therapeutically effective blood levels rapidly are particularly adapted for use in the invention. Examples of such drugs are: sedatives, hypnotics and antianxiety agents such as diazepam, midazolam, lorazipam and alprazolam; barbituates such as pentobarbital, and secobarbital; antihistamines such as hydroxyzines, diphenhydramine, phenothiazine, promethazine and propiomazine; buterophenones such as droperidol; opioids such as morphine, meperidine, fentanyl, sufentanyl, and alfentanyl; antiemetics such as droperidol, hydroxyzine, benzquinamide, scopolamine, and cyclizine; anticholinergic drugs such as atropine, scopolamine, and glycopyrrolate; and alpha 2 agonists such as clonidine and dexmedetomidine.

As used herein the term "flux" intends the rate of transfer of drug across skin as measured by the in vitro human cadaver skin tests described in *Medical Device and Diagnostic Industry* (1985) 8:35–42. The units of flux are preferably $\mu g/cm^2/hr$.

The term "volatile" that is herein used to describe certain permeation enhancers used in the invention intends compounds that enhance flux and have a vapor pressure greater than about 10 mm Hg at 25° C., preferably greater than about 30 mm Hg at 25° C. Correspondingly, the term "nonvolatile" that is used herein to describe certain other permeation enhancers used in the invention intends compounds that enhance flux and have a vapor pressure less than about 5 mm Hg at 25° C., preferably less than about 1 mm Hg at 25° C.

As used herein the term "initial pulse" intends a transient increase in flux relative to the baseline flux that is realized via administration of the drug from a reservoir lacking a volatile permeation enhancer. Such increase will usually be five- to ten-fold greater than said baseline flux. Correspondingly, the term "substantially lower" as used to characterize the flux after the initial pulse intends a flux that is typically 1 to 30%, more usually 10 to 20% of the maximum flux reached during the initial pulse. The initial pulse will normally last 0.5 to 8 hrs, more usually 1 to 4 hrs.

As used herein the term "administration period" intends the time period over which the device will deliver the drug at a rate that achieves and maintains the therapeutic, prophylactic or beneficial effect for which the drug is indicated. The administration period will usually be 1 to 7 days, more usually 1 to 3 days. The duration of the initial pulse in the flux will normally constitute 1 to 35%, more usually 10 to 20% of the administration period.

FIG. 1 depicts one embodiment, generally designated 10, of the invention device. Device 10 is in the form of a laminated composite having six components: (1) an uppermost impermeable backing layer 11 which forms the top surface of the device and which is removed from the device at the time the device is applied to the skin; (2) a permeable backing layer 12 that defines the top surface of the device during the administration period; (3) a confined drug reservoir 13 composed of a solution of drug in a carrier and a volatile permeation enhancer; (4) a permeable substrate layer 14 that is sealed to the backing layer 12 about the periphery of the reservoir 13; (5) a pressure-sensitive adhesive layer 15; and (6) a release liner layer 16 that is removed prior to placing the device on the skin.

The purpose of impermeable backing layer 11 is to prevent the volatile permeation enhancer from evaporating from the top of the device during storage. (The release liner layer plays a corresponding role at the opposite basal face of the device.) Accordingly, this layer is made of a material or combination of materials that is substantially impermeable to the enhancer and, preferably, the other components of the reservoir as well. It must also be capable of being removed from the remainder of the device so as to expose the underlying permeable backing 12 to the atmosphere. Examples of materials from which layer 11 may be made are metal foils, polycarbonate, polyesters, polytetrafluoroethylene, and polypropylene. The thickness of layer 11 is not critical. Its thickness will normally be in the range of 1 to 20 mm.

In an alternative embodiment of the invention, the impermeable backing may be eliminated by packaging the device so that the space within the package contains a sufficient amount of the volatile enhancer in vapor form to prevent the volatile enhancer in the reservoir from evaporating. In other words, the volatile enhancer vapor within the package is in equilibrium with the liquid form of the enhancer within the reservoir. In another alternative embodiment, the impermeable backing may be provided as an integral component of the package such that when the device is removed from the package the backing is left behind.

Permeable backing 12 underlies layer 11. As indicated, when layer 11 is removed, the thus exposed upper surface of layer 12 defines the top surface of the device. Backing layer 12 is sufficiently permeable to the volatile enhancer contained within the reservoir so as to permit essentially complete evaporation of the enhancer to occur within 0.1 to 10 hours, more usually 0.1 to 1 hour, from the time at which the impermeable backing and release liner are removed from the device and the device is placed on the skin.

Preferably layer 12 does not substantially absorb the drug or the other components of the reservoir while being permeable to the volatile enhancer. Layer 12 may be made from a dense (substantial absence of micro-or macropores) continuous material or from a porous or fibrous (e.g., nonwoven fabric) material that is capable of being sealed, preferably heat sealed, to the underlying substrate layer about the periphery of the reservoir. Preferably it is made of a polymeric material. Examples of dense or porous polymer films from which layer 12 may be made are microporous polyester and polyethylene. When dense or porous materials are used the thickness of layer 12 will typically be between 1 and 10 mm, more usually 2 to 5 mm. An example of a fibrous material from which the layer may be made is nonwoven polyester. Since layer 12 is permeable, it is noted that this device is nonocclusive (i.e., it permits transport of moisture and gases to and from the skin surface).

The drug reservoir 13 is confined between overlying layer 12 and underlying layer 14. As indicated the confinement may be accomplished by heat sealing layers 12 and 14 together about the periphery of the reservoir. The reservoir comprises the drug dissolved in a carrier (the drug may be present in excess, at saturation, or below saturation) and, at the time of placement on the skin, a volatile permeation enhancer. It should be noted that if the drug is a liquid at normal use temperatures, then a carrier is not required in the reservoir. The reservoir may also optionally contain a nonvolatile permeation enhancer. Depending upon the nature of the volatile permeation enhancer the concentration of the drug in the carrier may be affected by the presence of the volatile permeation enhancer. In this regard it is preferable that the volatile permeation enhancer be one that decreases the concentration of the drug in the carrier. The use of such a volatile permeation enhancer will cause the concentration of drug dissolved in the carrier to increase as the volatile enhancer evaporates from the reservoir. In this regard the initial pulse in the flux of drug through the skin results from the permeation enhancement effected by the volatile enhancer and, when the volatile enhancer is one that reduces the solubility of the drug in the carrier, from the increase of the solubility of the drug in the carrier as the volatile enhancer is depleted from the reservoir. The magnitude and duration of the pulse will depend upon the nature of the volatile enhancer (i.e., its ability to enhance flux and its vapor pressure), the amount of volatile enhancer in the reservoir, and the permeability of backing 12 to the volatile enhancer.

The flux following the initial pulse will be sufficient to maintain therapeutically effective levels of the drug in circulation for the desired administration period. The magnitude of that flux will depend on the permeability of the skin to the drug. That permeability may be enhanced by the inclusion of a nonvolatile permeation enhancer in the reservoir. In this regard the carrier itself may be a nonvolatile permeation enhancer, thus eliminating the necessity of adding a third component to the reservoir.

The amount of drug in the reservoir will depend upon the required rate of release of drug from the device and the intended lifetime of the device. Accordingly, the particular amount will vary from drug-to-drug. Normally the drug will constitute 1 to 20%, more usually 5 to 15% by weight of the reservoir. Correspondingly, the volatile permeation enhancer will normally constitute 65 to 95% by weight of the reservoir, more usually 75 to 85% by weight of the reservoir. When a separate nonvolatile enhancer is included in the reservoir (i.e., the carrier itself is not a nonvolatile enhancer) it will normally constitute 1 to 20% by weight, more usually 5 to 10% by weight of the reservoir.

Examples of carriers that are not permeation enhancers that may be used in the invention are mineral oil, propylene glycol, and silicone oil. Examples of carriers that are nonvolatile permeation enhancers are propylene glycol monolaurate (PGML), glycerol monooleate (GMO), oleic acid, and benzyl alcohol. The solubility of the drug in the carrier (whether affected or unaffected by the volatile enhancer) will usually be in the range of 50 to 100 mg/ml, more usually 70 to 90 mg/ml.

Examples of volatile enhancers that may be used in the reservoir are ethanol, isopropyl alcohol, ethyl ether, and acetone. Ethanol is preferred.

Substrate layer 14 merely serves as a structural layer to provide a basal wall that confines the reservoir. As such it is not a rate-controlling barrier to diffusion of drug from the reservoir to the skin. In other words, it is substantially more permeable to the drug than is the skin. Preferably it has an insignificant or no affect on release of drug from the reservoir to the skin. As indicated above, it is preferably made of a polymeric material that may be sealed to permeable backing 12 about the periphery of the reservoir. It is preferably made of a microporous material or a fibrous (e.g., nonwoven) material. Examples of such materials are nonwoven polyester, and microporous polyester or polypropylene. It is noted that the reservoir may be formulated as a nonflowable matrix (e.g., as a hydrogel). In such an instance a substrate layer is not required.

Pressure-sensitive adhesive layer 15 is the means by which the device is affixed to and maintained on the skin in a drug and permeation enhancer transferring relationship. Accordingly, the basal surface of layer 15 is in direct contact with the skin during use of the device and its area corresponds to the area of skin through which the drug passes. Like layer 14, layer 15 is not a rate-controlling barrier and has little, if any, affect on flux of drug or enhancer from the reservoir to the skin. It will normally be made of a drug-permeable polymer conventionally used as pressure-sensitive adhesives in transdermal drug delivery devices. Examples of such adhesives are polysiloxanes, polyacrylates, plasticized ethylene-vinyl acetate copolymers, low molecular weight polyester block amide copolymers (e.g., PEBAX copolymers), polyurethanes, and rubbery polyphers such as polyisobutene. If desired, this layer may also be loaded with drug.

In the embodiment of FIG. 1 substrate layer 14 and adhesive layer 15 provide a diffusive pathway for the drug and enhancer(s) to migrate from the reservoir to the skin. In alternative embodiments in which an inline adhesive layer is not used (e.g., such as use of a peripheral ring of adhesive, an adhesive overlay, straps, or other affixation means) to maintain the device on the skin, only substrate layer 15 is the diffusive pathway from the reservoir to the skin and the surface area of it in contact with the skin corresponds to the area of skin through which the drug is administered to circulation. In this regard that area (whether provided by the adhesive layer or the substrate layer) will typically be in the range of 10 $cm^2$ to 100 $cm^2$, more usually 20 $cm^2$ to 60 $cm^2$.

The release liner layer 16 is made of a conventional drug/enhancer impermeable polymer film (e.g., polyester) that is inherently strippable or rendered so by techniques such as silicone or fluorocarbon treatment.

The device of FIG. 1 may be made by conventional casting and lamination techniques. Commercially available films or nonwoven fabrics may be used for the impermeable backing, release liner, permeable backing and substrate layer. Commercially available pressure-sensitive adhesives may be used to make the adhesive layer. The reservoir components may be formulated by conventional mixing procedures, using gelling agents, if necessary, to provide a formulation of desired physical properties.

The following examples further illustrate the invention. These examples are not intended to limit the invention in any manner.

EXAMPLE 1

This example shows the invention used to administer the drug alprazolam (marketed under the name Xanax) which is indicated for treatment of anxiety, depression, and panic disorders. Unless indicated otherwise, percentages are by weight.

Adhesive was prepared by mixing 5% propylene glycol monolaurate (PGML) and 0.5% Xanax in silicone 2920 (Dow Corning) adhesive. The adhesive was coated onto a fluorocoated release liner using an 8 mil (2 mm) fixed-gap gardner knife. The adhesive was dried for 30 min at 70° C. to remove the solvent. The adhesive was then laminated to a piece of Celgard 2400 (microporous polypropylene) which serves as the heat-seal substrate. This laminate is referred to as the contact laminate.

The reservoir fluid was prepared by mixing 80% ethanol with 15% PGML and 5% Xanax. A second control reservoir fluid was formulated by mixing 15% ethanol with 80% mixed vegetable oils (MVO, a mixture of natural soybean and coconut oils) and 3% Xanax. The mixtures were agitated until clear solutions were obtained.

The contact laminate was adhered to the skin for in vitro testing and the reservoir fluid was pipetted onto the top of the laminate. This mimics the effect of manufacturing a complete device or patch.

Modified Franz vertical cells were used for in vitro skin permeation studies which were carried out to determine the burst effect. The release liner was peeled off the system and the foil impermeable backing was also removed immediately prior to placing the system on heat-separated human epidermis. The epidermis and patch were then mounted between the donor and receiver compartments and clamped in place. The receiver compartments were filled with phosphate buffer and the temperature was maintained at 32° C. Samples were taken at preset intervals and assayed by HPLC.

Figure 2:
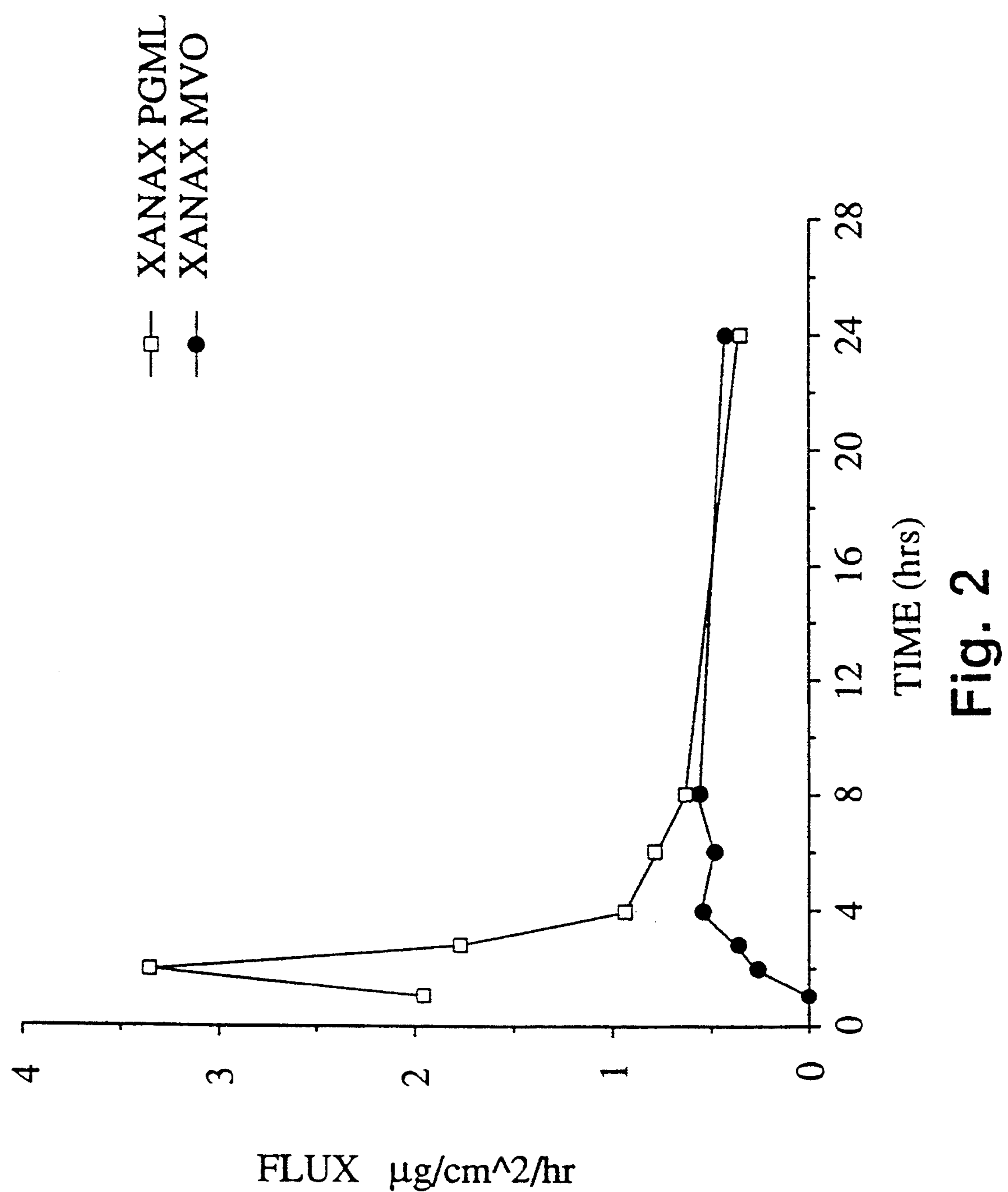
FIG. 2 is a graph showing the in vitro flux of xanax versus time, as determined pursuant to Example 1 infra.

The results of the tests are shown graphically in FIG. 2. As shown the invention device exhibited an initial pulse influx whereas the control device did not exhibit an initial pulse.

EXAMPLE 2

This example shows the use of the invention to deliver the drug dexmedetomidine.

Adhesive was prepared by mixing 5% PGML and 0.5% dexmedetomidine in silicone 2920 (Dow Corning) adhesive. The adhesive was coated onto a fluorocoated release liner using an 8 mil (2 mm) fixed-gap gardner knife. The adhesive was then laminated to a piece of Celgard 2400 (microporous polypropylene) which serves as the heat seal substrate. This laminate is referred to as the contact laminate.

The backing laminate was prepared by heat-laminating Reynolds foil 720 (1 mil foil with a heat-seal coating) to Reemay 2250 (nonwoven polyester). This heat seal is nondestructive, i.e., the materials may be separated without destroying them.

The reservoir fluid was prepared by mixing 80% ethanol with 20% PGML. One hundred mg/g of dexmedetomidine was added and the mixture was agitated until a clear solution was obtained.

The backing laminate is then destructively heat-sealed to the contact laminate (nonwoven in contact with the heat-seal substrate) around three sides of the patch. A 2-inch-by-1.5-inch piece of the nonwoven was placed into the patch through the open side to act as a sponge and hold the reservoir fluid (this has no effect on patch function but makes manufacturing easier). Two hundred ninety microliters of the reservoir fluid was pipetted into each patch through the open side. The open side is then heat-sealed closed to contain the fluid.

Figure 3:
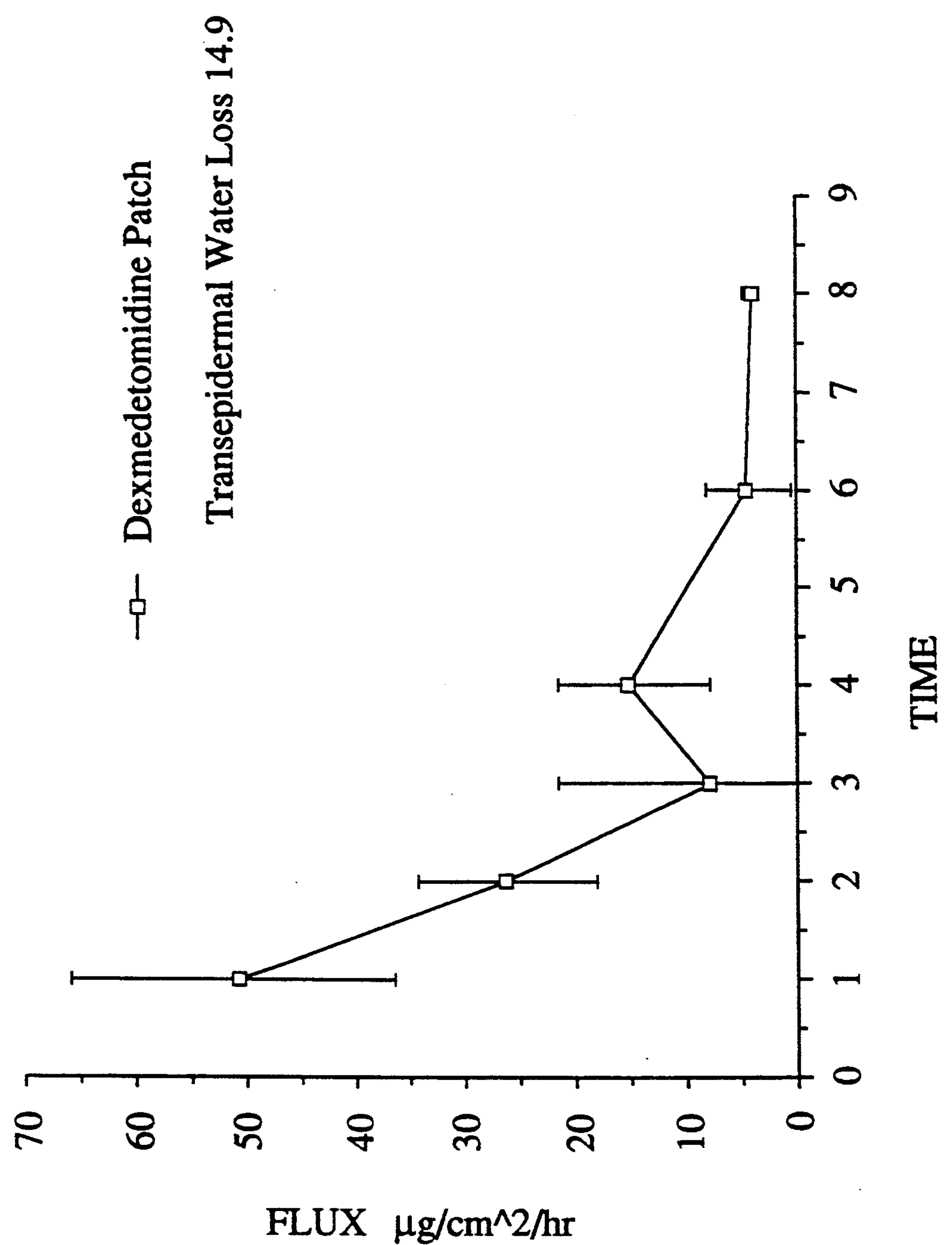
FIGS. 3 and 4 are graphs showing the in vitro flux of dexmedetomidine versus time, as determined pursuant to Examples 2 and 3 infra.

Modified Franz vertical cells were used for in vitro skin permeation studies which were carried out to determine the burst effect. The release liner was peeled off the system and the foil impermeable backing was also removed immediately prior to placing the system on heat-separated human epidermis. The epidermis and patch were then mounted between the donor and receiver compartments and clamped in place. The receiver compartments were filled with phosphate buffer, pH 5.0 and the temperature was maintained at 32° C. Samples were taken at preset intervals and assayed by HPLC. The results of these tests are shown in FIG. 3.

Modifications of the above-described modes for carrying out the invention that are obvious to those of skill in the fields of transdermal drug delivery devices are intended to be within the scope of the following claims.

EXAMPLE 3

This example also shows the use of the invention to administer desmedetomidine. As compared to Example 2, no drug or PGML was added to the adhesive layer in this example.

The adhesive was coated onto a fluorocoated release liner using an 8 mil (2 mm) fixed-gap gardner knife. The adhesive was dried for 30 minutes at 70° C. to remove the solvent. The adhesive was then laminated to a piece of Celgard 2400 (microporous polypropylene) which serves as the heat-seal substrate. This laminate is referred to as the contact laminate.

The backing laminate was prepared by heat-laminating Reynolds foil 720 (1 mil foil with a heat-seal coating) to Reemay 2250 (nonwoven polyester). This heat seal is nondestructive, i.e., the materials may be separated without destroying them.

The reservoir fluid was prepared by mixing 80% ethanol with 20% propylene glycol monolaurate. One hundred mg/g of dexmedetomidine was added and the mixture was agitated until a clear solution was obtained.

The backing laminate is then destructively heat-sealed to the contact laminate (nonwoven in contact with the heat-seal substrate) around three sides of the patch. A 2-inch-by-1.5-inch piece of the nonwoven was placed into the patch through the open side to act as a sponge and hold the reservoir fluid (this has no effect on patch function but makes manufacturing easier). Two hundred ninety microliters of the reservoir fluid was pipetted into each patch through the open side. The open side is then heat-sealed closed to contain the fluid.

Modified Franz vertical cells were used for in vitro skin permeation studies which were carried out to determine the burst effect. The release liner was peeled off the system and the foil impermeable backing was also removed immediately prior to placing the system on heat-separated human epidermis. The epidermis and patch were then mounted between the donor and receiver compartments and clamped in place. The receiver compartments were filled with phosphate buffer and the temperature was maintained at 32° C. Samples were taken at preset intervals and assayed by HPLC.

Figure 4:
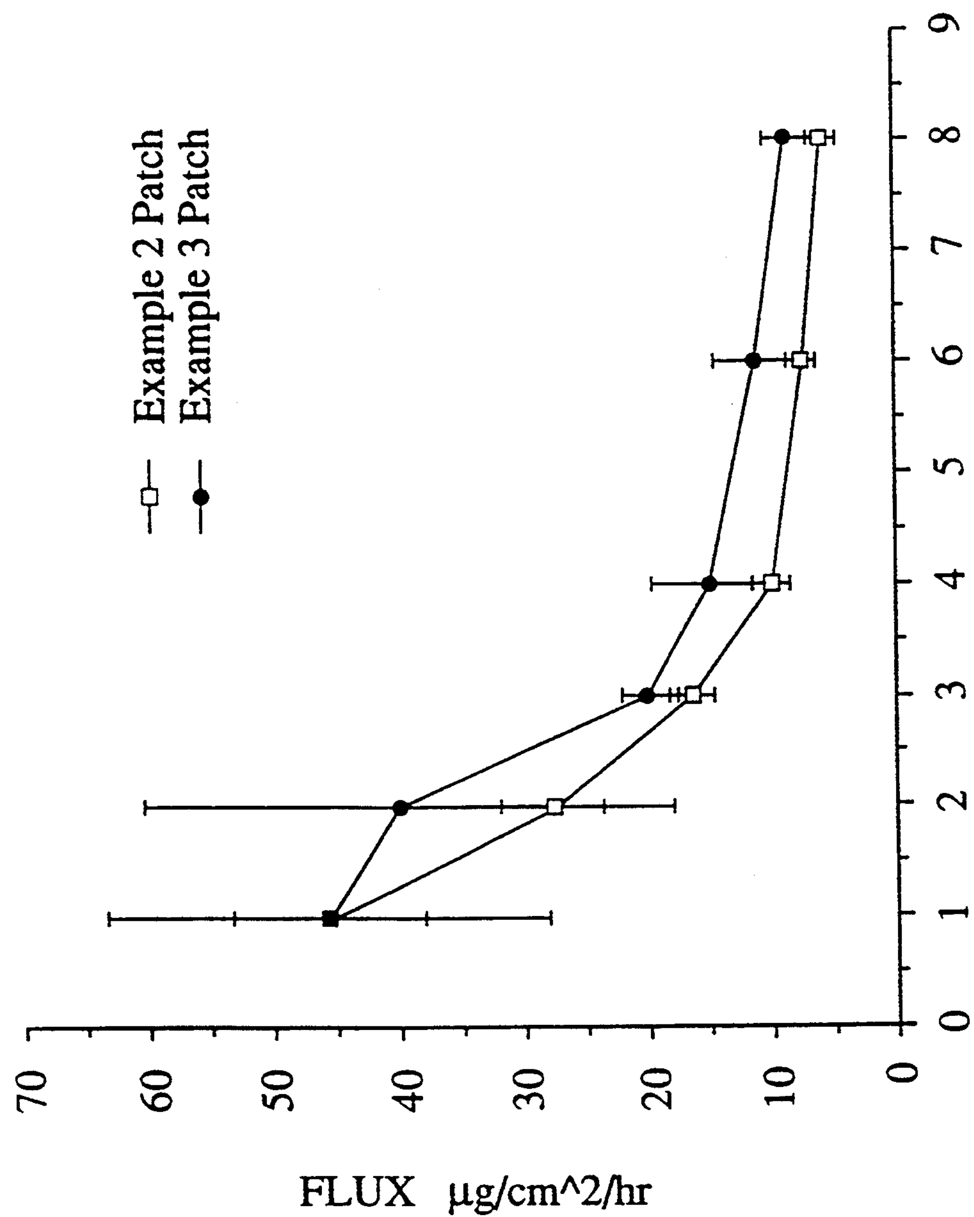

The results of these tests are shown in FIG. 4. For comparison purposes the flux from the device of Example 2 is included in FIG. 4.

Modifications of the above-described modes for carrying out the invention that are obvious to those of skill in the fields of chemistry, transdermal drug delivery, pharmacology, and related fields are intended to be within the scope of the following claims.

We claim:

1. A device for administering a drug through intact skin that provides an initial pulse in the flux of the drug through the skin followed by a substantially lower flux of drug through the skin comprising in combination:

(a) a reservoir comprising the drug and a volatile permeation enhancer having a vapor pressure greater than about 10 mm Hg at 25 ° C.;

(b) a backing layer overlying the reservoir that is permeable to the volatile permeation enhancer such as to permit essentially complete evaporation of the enhancer to occur within 0.1 to 10 hours from the time at which the said permeable backing layer is exposed to the atmosphere, and (c) means for maintaining the device on the skin in drug and permeation enhancer transferring relationship thereto, whereby when the device is placed on the skin, the volatile permeation enhancer is depleted from the reservoir by evaporation through the backing layer with the magnitude and duration of the pulse being dependent among other things upon the permeability of the backing layer to the enhancer.

2. The device of claim 1 wherein the drug is dissolved in a carrier and the reservoir is confined between the backing layer and an underlying layer that provides a diffusive pathway for the drug and enhancer to migrate from the reservoir to the skin.

3. The device of claim 1 wherein the reservoir includes a nonvolatile permeation enhancer.

4. The device of claim 2 wherein the carrier is a nonvolatile permeation enhancer.

5. The device of claim 2 wherein the concentration of drug in the carrier increases as the volatile permeation enhancer evaporates from the device.

6. The device of claim 4 wherein the concentration of drug in the carrier increases as the volatile permeation enhancer evaporates from the device.

7. The device of claim 2 wherein the volatile permeation enhancer constitutes 65 to 95% by weight of the reservoir and the drug and carrier constitute the remainder of the reservoir.

8. The device of claim 1 wherein the backing layer is made of a nonwoven polymer fabric.

9. The device of claim 8 wherein the fabric does not absorb the drug and the carrier.

10. The device of claim 1 wherein said means is an in-line layer of a pressure-sensitive adhesive.

11. The device of claim 2 wherein the carrier is propylene glycol monolaurate and the volatile permeation enhancer is ethanol.

12. The device of claim 1 wherein the drug is dexmedetomidine.

13. The device of claim 2 wherein the drug is dexmedetomidine.

14. The device of claim 2 wherein the drug is dexmedetomidine and constitutes 1 to 20% by weight of the reservoir, the carrier is propylene glycol monolaurate and constitutes 1 to 20% by weight of the reservoir, the volatile permeation enhancer is ethanol and constitutes 65 to 95% by weight of the reservoir, the backing layer is nonwoven polyester fabric, the underlying layer is a microporous membrane, and said means is an in-line layer of a polysiloxane adhesive.

15. A method for administering a drug transdermally wherein there is an initial pulse in the flux of the drug through the skin followed by a substantially lower flux of drug through the skin comprising:

(a) applying a formulation of the drug and a volatile permeation enhancer having a vapor pressure greater than about 10 mm Hg at 25° C. to the skin wherein the formulation is covered by a backing that is permeable to the volatile permeation enhancer;

(b) permitting the volatile permeation enhancer to evaporate from said formulation through said backing whereby the magnitude and duration of the pulse is determined by inter alia the permeability of the backing to the volatile permeation enhancer.

16. The device of claim 1 wherein the volatile permeation enhancer is ethanol, isopropylalcohol, ethyl ether, or acetone.

17. The device of claim 15 wherein the volatile permeation enhancer is ethanol, isopropylalcohol, ethyl ether, or acetone.

* * * * *